(12) United States Patent
Gao et al.

(10) Patent No.: US 6,869,758 B1
(45) Date of Patent: Mar. 22, 2005

(54) METHOD AND DEVICE FOR REMOVAL OF CRYOPROTECTANT FROM CRYOPRESERVED BIOLOGICAL CELLS AND TISSUES

(75) Inventors: Dayong Gao, Lexington, KY (US); XiangDong Cui, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 107 days.

(21) Appl. No.: 10/206,539

(22) Filed: Jul. 26, 2002

Related U.S. Application Data

(60) Provisional application No. 60/307,984, filed on Jul. 26, 2000.

(51) Int. Cl.$^7$ ............................. A01N 1/00; A01N 1/02; C12N 5/00
(52) U.S. Cl. ........................ 435/1.1; 435/1.2; 435/1.3; 435/2; 435/325
(58) Field of Search ........................... 435/1.1, 1.2, 1.3, 435/2, 325

(56) References Cited

U.S. PATENT DOCUMENTS

| | | |
|---|---|---|
| 5,691,133 A | 11/1997 | Critser et al. |
| 5,700,632 A | 12/1997 | Critser et al. |
| 5,753,427 A | 5/1998 | Critser et al. |
| 5,776,769 A | 7/1998 | Critser et al. |
| 5,879,876 A | 3/1999 | Wolfinbarger, Jr. et al. |
| 6,054,287 A | 4/2000 | Gao et al. |
| 6,068,775 A * | 5/2000 | Custer et al. ............... 210/638 |
| 6,124,088 A | 9/2000 | Amann et al. |
| 6,326,188 B1 | 12/2001 | Wolfinbarger, Jr. et al. |
| 6,399,363 B1 | 6/2002 | Hammerstedt et al. |

OTHER PUBLICATIONS

Kennard et al., "Membrane anchored protein production from spheroid, porous, and solid microcarrier Chinese hamster ovary cell cultures", Biotechnology and Bioengineering 47 (5) : 550–556 (1995).*

* cited by examiner

*Primary Examiner*—Sandra E. Saucier
(74) *Attorney, Agent, or Firm*—King & Schickli, PLLC

(57) ABSTRACT

Novel methods and devices for removing cryoprotectant from cryoprotectant-containing liquids, and from cells residing therein, are disclosed. In one aspect, the method comprises passing the cryoprotectant-containing liquid through at least one semipermeable hollow fiber membrane contained in a hollow module in a first direction, while passing a liquid which is substantially free of cryoprotectant through the hollow module in a second direction to remove cryoprotectant across a diffusion gradient. In another aspect, a device is described for removing cryoprotectant from a liquid, comprising a hollow module with at least one semipermeable hollow fiber membrane therein for accomplishing such counter-current diffusion removal of cryprotectant. A software program is also provided for predicting optimal flow rates through the device of the invention, thereby allowing optimal cryoprotectant removal regardless of the cryoprotectant used or the material from which the semipermeable hollow fiber membrane is fabricated.

18 Claims, 3 Drawing Sheets

US 6,869,758 B1

METHOD AND DEVICE FOR REMOVAL OF CRYOPROTECTANT FROM CRYOPRESERVED BIOLOGICAL CELLS AND TISSUES

This application claims the benefit of U.S. Provisional Patent Application Ser. No. 60/307,989, filed Jul. 26, 2001.

This invention was made with partial Government support under NSF grant no. DMI-9901698. The Government may have certain rights in this invention.

TECHNICAL FIELD

The present invention relates to methods for removal of cryoprotectant from suspensions of cryopreserved biological cells and tissues following thawing. The invention more specifically relates to a perfusion-washing method and device for removal of cryoprotectant from cryopreserved biological cells and tissues following thawing.

BACKGROUND OF THE INVENTION

It is known to utilize various cryoprotectants, such as for example dimethyl sulfoxide, during cryopreservation of cells. Use of a cryoprotectant is essential to prevent cryoinjury from, e.g., formation of intracellular ice crystals during freezing. However, at room and/or body temperature, certain cryoprotectants such as DMSO are known to be toxic to cells. Accordingly, cryoprotectant must be removed from cryopreserved cell cultures as soon as possible after thawing to prevent cellular damage.

The most common method for removal of cryoprotectant from cryopreserved cells is by mechanical removal, i.e. centrifugation followed by resuspension in the media of choice to remove the cryoprotectant by dilution. However, the mechanical forces introduced during centrifugation result in osmotic stress and cell clumping/lysing, particularly if the cell of choice is fragile. The generally open nature of most centrifugation processes may also result in bacterial or viral contamination of cell preparations. Accordingly, there is need in the art for a method of removing cryoprotectant which does not result in cell damage or risk contamination of cell preparations. The instant invention satisfies this need by providing a method and device for removing cryoprotectant using a counter-current perfusion washing system.

SUMMARY OF THE INVENTION

In accordance with the purposes of the present invention as described herein, in one aspect of the present invention a method is provided for removing a cryoprotectant from an interior of a cell immersed in a cryoprotectant-containing liquid, comprising the steps of passing the cryoprotectant-containing liquid through at least one semipermeable hollow fiber membrane contained in a hollow module in a first direction to contact said hollow fiber membrane on at least one interior surface. Concurrently, a liquid which is substantially free of cryoprotectant is passed through the hollow module in a second direction (opposite to the first direction) so that the cryoprotectant-free liquid contacts the semipermeable hollow fiber membrane on at least one exterior surface. It will be appreciated that a diffusion gradient is created, thereby transferring the cryoprotectant from the cryoprotectant-containing liquid to the cryoprotectant-free liquid for removal.

The method of the present invention is suitable for use on cryopreserved cells contained in suspension. Similarly, the method is suitable for cryopreserved tissue blocks, for monolayer cell cultures, and for so-called "bioreactors", wherein the cells of interest are seeded in a substantially solid growth matrix for growth prior to immersion in the cryoprotectant-containing liquid. It will be appreciated that cells in suspension in cryoprotectant-containing liquid may be directly passed through the semipermeable hollow fiber membrane of the present invention. For cells grown in or on solid matrices, such as tissue blocks or bioreactors in a cell culture dish, cryoprotectant-containing liquid cell culture media may be removed from the cell culture dish, passed though the semipermeable hollow fiber membranes as described to remove cryoprotectant, and returned to the cell culture dish.

Any semipermeable hollow fiber membrane capable of allowing passage of a cryoprotectant therethrough while preventing passage of cells is suitable for the method of this invention. In one presently preferred embodiment, a semipermeable hollow fiber membrane having a porosity of from about 50% to about 80% is used. Typically, a semipermeable hollow fiber membrane having a porosity of about 70% is used.

In accomplishing the method of the present invention, a first flow rate for passing cryoprotectant-containing liquid through the interior of the semipermeable hollow fiber membrane is selected to be sufficient to allow diffusion of the cryoprotectant from the interior of the membrane to the exterior. The second flow rate for removing cryoprotectant from the exterior surface of the membrane is selected to be sufficient to allow removal of cryoprotectant from the exterior surface of the membrane to prevent fouling of the exterior of the membrane fiber.

In another aspect, a method for removing a cryoprotectant from an interior of a cell immersed in a cryoprotectant-containing liquid is provided. The method comprises the steps of: (1) determining the membrane transfer potential of a chosen semipermeable hollow fiber membrane material for a cryoprotectant of choice; (2) calculating a first flow rate based on the membrane transfer potential for passing the cryoprotectant-containing liquid through the semipermeable hollow fiber membrane; (3) calculating a second flow rate based on the membrane transfer potential for passing a cryoprotectant-free liquid through the hollow module; (4) passing the cryoprotectant-containing liquid through at least one semipermeable hollow fiber membrane contained within the hollow module at the calculated first flow rate in a first direction to contact the hollow fiber membrane on at least one interior surface; (5) passing the cryoprotectant-free liquid at the second flow rate through the hollow module in a second direction opposite to the first direction so that the cryoprotectant-free liquid contacts the semipermeable hollow fiber on at least one exterior surface; and (5) transferring cryoprotectant from the cryoprotectant-containing liquid to the cryoprotectant-free liquid across a diffusion gradient created between the interior surface and the exterior surface of the semipermeable hollow fiber.

It will be appreciated that the membrane transfer potential of a particular material from which the semipermeable hollow fiber is fabricated is known for many suitable materials, or may be determined by experimentation. As noted above, the method is suitable for removing cryoprotectant from cells any state, such as in suspension, in tissue blocks, in monolayer culture, and seeded in bioreactors. The characteristics of the semipermeable hollow fiber membranes and the desired first and second flow rates are as described above.

In accomplishing the methods of the present invention, the first and second flow rate will be calculated in accordance with the membrane transfer potential of the semipermeable hollow fiber membrane for the cryoprotectant of choice. Thus, it will be appreciated that the method of this invention may be tailored specifically to optimal removal of a particular cryoprotectant from a particular cell culture media.

In yet another aspect of this invention, a device for removing cryoprotectant from an interior of a cell immersed in a cryoprotectant-containing liquid is provided, comprising a hollow module, at least one semipermeable hollow fiber membrane contained within an interior of the hollow module, a means for passing the cryoprotectant-containing liquid through the semipermeable hollow fiber membrane in a first direction, and a means for passing a substantially cryoprotectant-free liquid through the exterior hollow module in a second direction opposite to the first direction. The device is suitable for removing cryoprotectant from cells in any state, such as in suspension, in tissue blocks, in monolayer culture, and seeded in bioreactors. The characteristics of the semipermeable hollow fiber membranes and the desired first and second flow rates are as described above.

Any suitable means may be employed for passing liquid through the semipermeable hollow fiber membrane and the hollow module may be used, such as a peristaltic pump, a syringe pump, or the like. The device may comprise a closed system, wherein cells in cryoprotectant-containing liquid are recirculated through the semipermeable hollow fiber membrane and cryoprotectant-free liquid is recirculated through the hollow module, or may be an open system wherein only a single passage of cells/cryoprotectant-containing liquid and cryoprotectant-free liquid are used.

Other objects and applications of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Reference will now be made in detail to a presently preferred embodiment of the invention, examples of which are illustrated in the accompanying drawing.

DETAILED DESCRIPTION OF THE INVENTION

Figure 1:
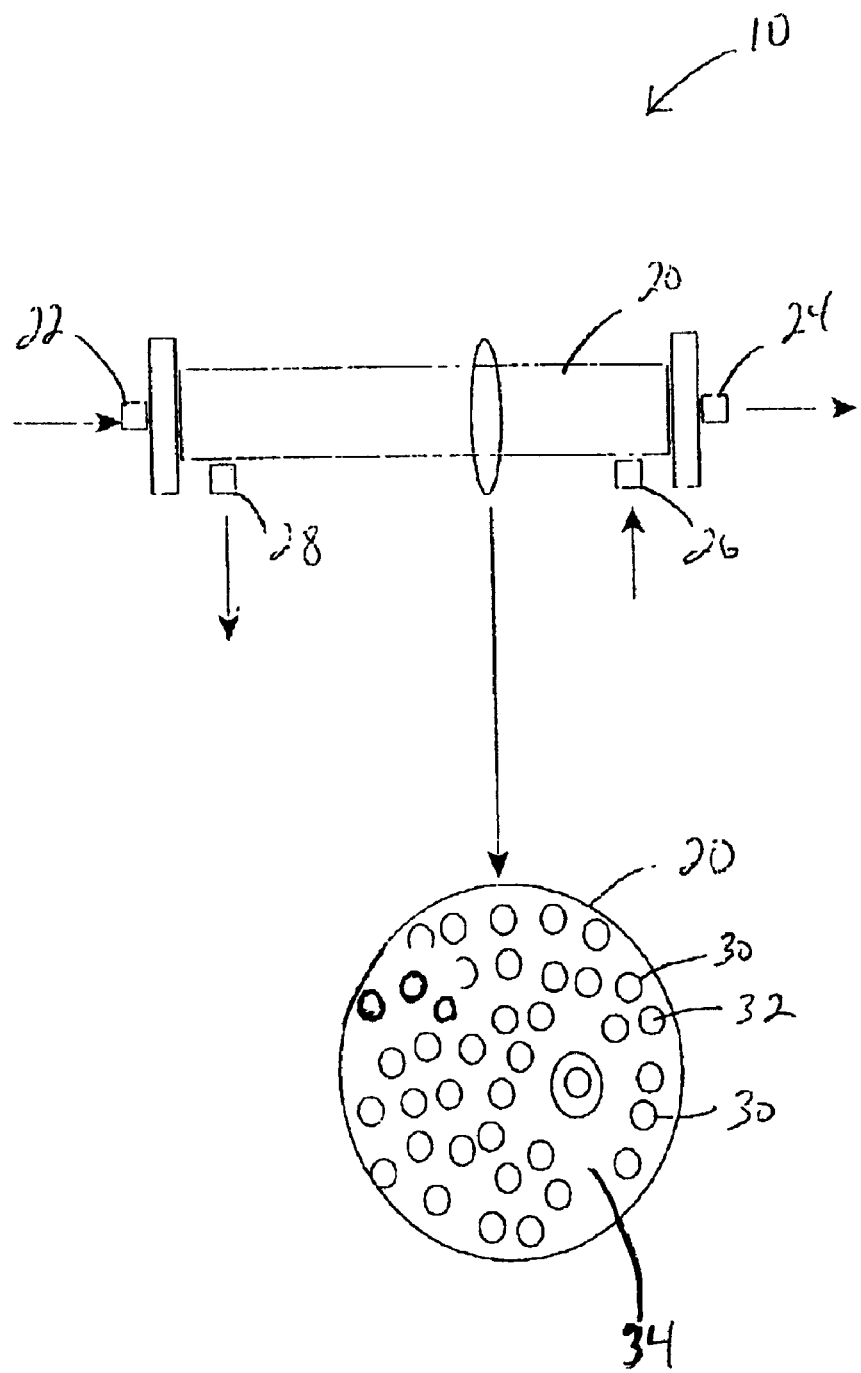
FIG. 1 shows a schematic representation of the device of the present invention, with the semipermeable hollow fiber membranes shown schematically in the interior of the hollow module in cross-section.

As shown schematically in FIG. 1, the method of the present invention comprises passage of a cryoprotectant-containing liquid in a first direction through hollow, semiporous membrane fibers contained in a hollow module in such a way as to contact an internal surface of the fibers. Suitable hollow, semi-permeable fibers and cylindrical modules are known in the art, particularly in the dialysis arts. Cryoprotectant-free liquid is passed through the hollow module in a second direction, opposite to the first direction, in such a way as to contact an external surface of the fibers. The device 10 of the invention comprises a hollow module 20 having a first inlet 22 and a first outlet 24 for cryoprotectant-containing liquid, and a second inlet 26 and a second outlet 28 for cryoprotectant-free liquid. As shown in partial cross-section, the hollow module 20 includes a plurality of semipermeable hollow fiber membranes 30, each having a lumen 32. Cryoprotectant-containing liquid is passed through inlet 22, through the lumens 32 of each membrane 30, and out outlet 24. Concurrently, cryoprotectant-free liquid is passed into hollow module 20 through inlet 26, through a space 34, contacting the exterior of hollow fiber membranes 30, and out outlet 28. Any suitable means, such as syringe pumps or peristaltic pumps (not shown) may be used to effect fluid flow through the device of the invention.

It will be appreciated that, by selection of appropriate hollow, semipermeable fibers, a diffusion gradient is established whereby cryopreservant flows from the cryoprotectant-containing liquid (containing a relatively high concentration of cryoprotectant) to the cryoprotectant-free liquid (containing a relatively low concentration of cryoprotectant). When this counter-flow perfusion technique is used, cryopreservant diffuses from the cyoprotectant-containing liquid contained in the inner portion of the hollow fibers into the cryoprotectant-free liquid. In a closed system, the cryoprotectant-containing liquid may be recirculated through the hollow, semipermeable membrane fibers until the desired amount of cryopreservant is removed. It will be appreciated that the cryoprotectant-free liquid may be supplied in either a closed or an open system (comprising discarding cryoprotectant-free liquid after a single passage through the hollow module).

EXAMPLE 1

In accordance with the methods of the invention, a cylindrical module as described above was loaded with 500 cellulose-triacetate fibers (internal diameter 100 $\mu$m; membrane thickness 15 $\mu$m; porosity 70%). Hematopoietic progenitor cells (HPCs) derived from umbilical cord blood and cryopreserved in a solution containing 10% DMSO, were passed through the cellulose-triacetate fibers in a first direction. Isotonic perfusion media (substantially free of cryoprotectant) was passed through the cylindrical module in a second direction, directly opposite to the first direction, in such a way as to contact the outer surface of the fibers. The cell suspension was recirculated through the fibers by automated pumps in a closed system until over 95% of the original concentration of DMSO was removed.

Figure 2:
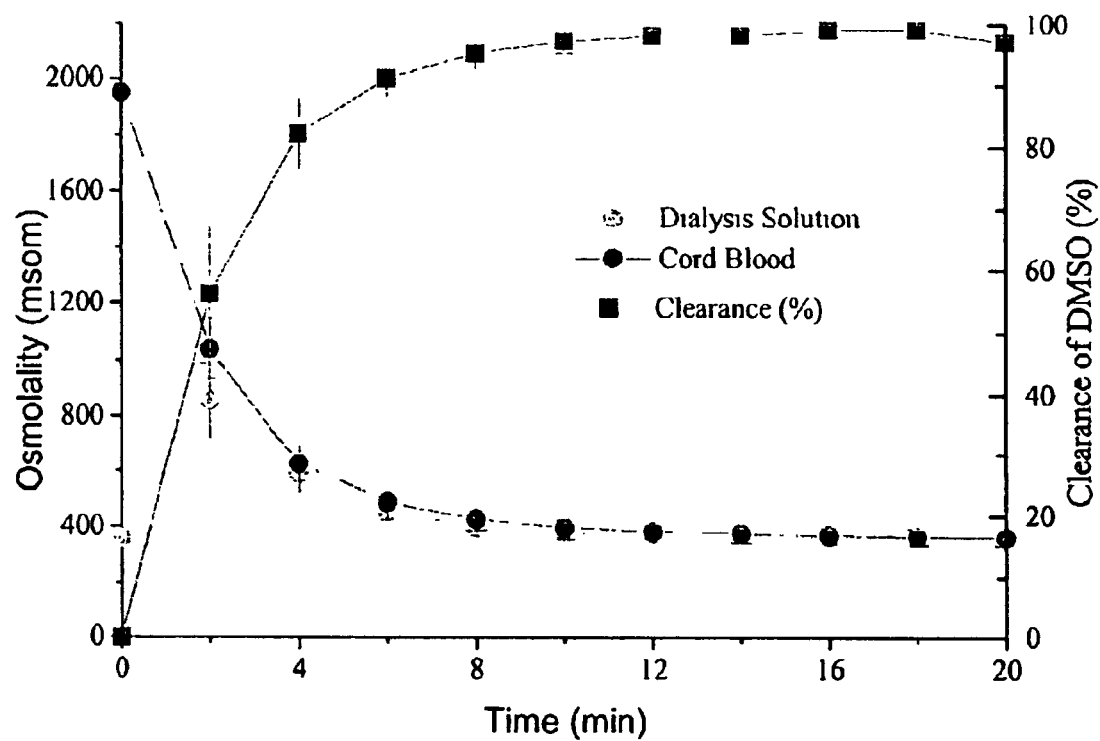
FIG. 2 shows changes in osmolality of cord blood with DMSO and in cryoprotectant-free perfusion solution, and percent clearance of DMSO from cord blood as a function of time of washing.

As best seen in FIG. 2, on the basis of calculated changes in total osmolality, percent DMSO clearance, and change in osmolality of the perfusion washing medium, over 95% of the DMSO in the cryopreserved blood sample was removed by the method and device of the instant invention within 5 minutes of initiation of the washing process. No cell clumping was observed.

EXAMPLE 2

Fresh umbilical cord blood samples were mixed with cryoprotectant solution (20% DMSO v/v, 10% citratephosphate double dextrose [CP2D] v/v, and 70% phosphate-buffered saline v/v) in a 1:1 ratio (final concentration of DMSO=10% v/v). The umbilical cord blood samples were then cooled and cryopreserved. After 1 week storage in liquid nitrogen, the cells were thawed. Samples of the blood were subjected to standard centrifugation/washing techniques and to the novel perfusion washing method of the present invention as described in Example 1 supra.

As best seen in Table 1, cell function survival was significantly enhanced in cell preparations subjected to the method of the present invention (compared to standard centrifugation washing) for removal of DMSO. Flow cytometry studies (not shown) conducted using methods known in the art showed that recovery of CD34+cells was 92% for the method of this invention, in comparison to 80% recovery of CD34+cells for centrifugation washing.

TABLE 1

Cell function survival (%, in comparison with the fresh control) with different cell washing approaches (centrifugation vs. dialysis, N = 8)

|  | CFU-E | BFU-E | CFU-GM |
| --- | --- | --- | --- |
| Centrifuge | 11.3 ± 4.1% | 27.3 ± 2.2% | 49.3 ± 5.1% |
| Dialysis | 45.0 ± 3.2% | 47.9 ± 7.3% | 72.5 ± 4.5% |

Accordingly, the method and device of the present invention provides a reliable, effective means for removing cryoprotectant from cell suspensions which significantly reduces cell clumping, cell lysis, loss in viability, and osmotic injury. The method is suitable for removal of cryoprotectant of numerous useful cell types, including bone marrow/cord blood hematopoietic progenitor cells for cancer treatment and gene therapy, for tissue cryopreservation for transplantation, for sperm/oocyte preservation for artificial insemination and in vitro fertilization, for cryopreservation of cell lines for research, and the like.

It will be appreciated that the method and device of this invention is equally suited to removal of cryoprotectant from cells cryopreserved other than in suspension. For example, it is known to culture and cryopreserve cells by seeding in "bioreactors" comprising a porous growth matrix such as polyglycolic acid polymers, polylactic acid polymers, collagen, and the like. The method of the present invention may easily be adapted for such cultures by simply extracting the cryoprotectant-containing media bathing the porous growth matrix in the cell culture vessel, passing it through the semipermeable hollow fiber membranes of the invention, and returning the media, now free of cryoprotectant, to the cell culture vessel.

In still another aspect of the present invention, a method for determining optimum operating conditions of the device of the present invention for removal of cryoprotectant is provided. It has been discovered that the first, cell/cryoprotectant liquid flow rate may be accurately predicted using Navier-Stokes equations. Flow rate of the second, cryoprotectant-free liquid may be accurately predicted using Darcy equations. Permeating flow through the semipermiable, hollow fiber membrane for a particular cryoprotectant may be accurately predicted using Kedem-Katchalsky equations.

Darcy's law describes the relationship between volume average velocity and gradient of volume average pressure:

$$u_r = -\frac{1}{\mu} k_{rr} \frac{\partial p}{\partial r} \quad u_z = -\frac{1}{\mu} k_{zz} \frac{\partial p}{\partial z} \tag{1}$$

where $K_{rr}$ and $K_{zz}$ are Darcy permeability in r and z direction respectively.

The volume average conservation of mass equation is:

$$\frac{1}{r} \frac{\partial (r u_r)}{\partial r} + \frac{\partial u_z}{\partial z} = -S_m \tag{2}$$

Inserting eq.(1) into eq.(2), gives:

$$\frac{1}{r} \frac{\partial}{\partial r}\left(\frac{1}{\mu} k_{rr} r \frac{\partial p}{\partial r}\right) + \frac{\partial}{\partial z}\left(\frac{1}{\mu} k_{zz} \frac{\partial p}{\partial z}\right) = S_m \tag{3}$$

If $K_{rr}$, $K_{zz}$ and $\mu$ are constant, eq.(3) can be simplified as:

$$\frac{1}{r} \frac{k_{rr}}{\mu} \frac{\partial}{\partial r}\left(r \frac{\partial p}{\partial r}\right) + \frac{k_{zz}}{\mu} \frac{\partial^2 p}{\partial z^2} = S_m \tag{4}$$

Considering a fluid control volume, whose cross section area is A and length is $\Delta z$. The number of hollow fibers $N_H$ may be estimated in this control volume by $$N_H = \frac{A \cdot f}{A_H} \tag{5}$$

where $A_H$ is the cross sectional area of one hollow fiber, and $f$ is packing density. Then membrane area $A_m$ in this control volume can be determined by $$A_m = N_H \pi d_H \cdot \Delta z \tag{6}$$

where $d_H$ is the diameter of hollow fiber.
Therefore, $S_m$ may be calculated by $$S_m = \frac{J_v \cdot A_m}{A \cdot \Delta z} \tag{7}$$

where $J_v$ is the ultrafiltration rate, which can be calculated by Kedem-Katchalsky equation (K—K equation):

$$J_v = L_p \cdot \Delta p - \sigma L_p RT \cdot \Delta C \tag{8}$$

where $\Delta p$ is the difference of pressure between cryoprotectant-containing liquid and cryoprotectant-free liquid, $\Delta c$ is the difference of concentration between cryoprotectant-containing liquid and cryoprotectant-free liquid, $L_p$ is the hydraulic permeability of membrane, $\sigma$ is reflection coefficient, T is temperature, and R is universal gas constant.

Neglecting mass transfer by shell-side diffusion or Taylor dispersion relative to convection, the equation of concentration can be written as:

$$u_r \frac{\partial C}{\partial r} + u_z \frac{\partial C}{\partial z} = S_s \tag{9}$$

where C is the cryoprotectant concentration, and $S_s$ is the cryoprotectant source. The cryoprotectant concentration in the cryoprotectantfree liquid increases from inlet to outlet, while cryoprotectant concentration in cryoprotectant-containing liquid decreases from sample inlet to outlet.

$S_s$ can be estimated by $$S_s = \frac{J_s \cdot A_m}{A \cdot \Delta \xi},$$

where $J_s$ is solute flux across the membrane. K—K equation can be used to calculate $J_s$:

$$J_s = C_s^*(1-\sigma)J_v + P_s \cdot \Delta C_s \quad (10)$$

where $c_s^*$ is average of solute concentration inside membrane, $P_s$ is solute diffusive permeability of membrane.

In a typical configuration of the device of the present invention, a bundle of semipermeable hollow fiber membranes is contained in a hollow module and encapsulated at each end forming tubesheets. At each end, a gasket and endcap form headers to direct sample flow in and out of the lumens of the fibers. Accordingly, the sample flow is more uniform than cryoprotectant-free liquid flow. In our model, the flow rate in the inlet of each fiber membrane is assumed to be the same. Using Navier-Stokes equations to simulate the sample flow:

Continuity Equation:

$$\nabla \cdot u = 0 \quad (11)$$

Momentum Equations:

$$u \cdot \nabla u_r = -\frac{1}{\rho}\frac{\partial p}{\partial r} + \frac{\mu}{\rho}\nabla^2 u_r \quad (12)$$

$$u \cdot \nabla u_z = -\frac{1}{\rho}\frac{\partial p}{\partial z} + \frac{\mu}{\rho}\nabla^2 u_z \quad (13)$$

Concentration Equation:

$$u \cdot \nabla C = D \nabla^2 C \quad (14)$$

where u is the velocity vector: $u = (U_r, u_z)$.

Figure 3:
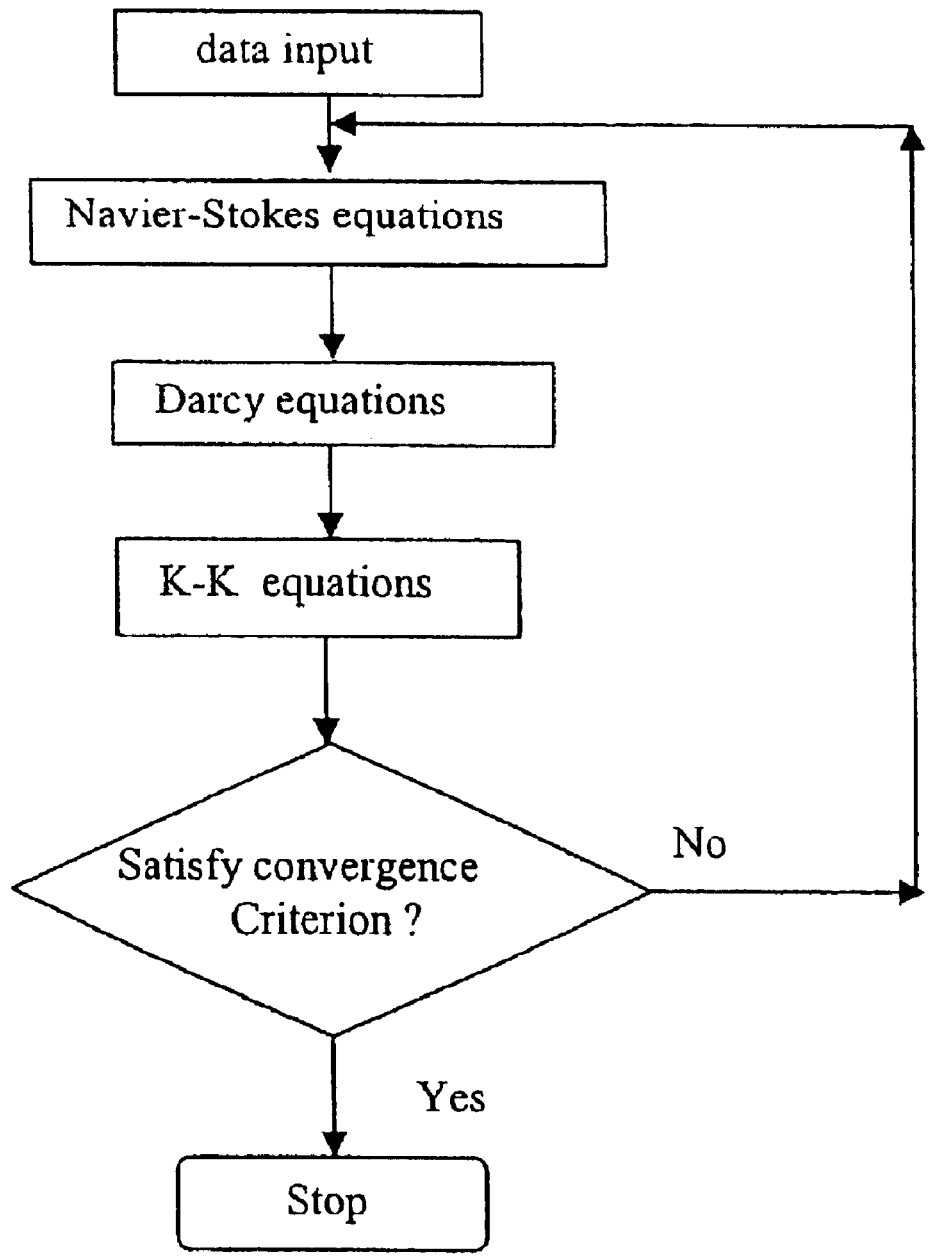
FIG. 3 shows a schematic representation of the calculations performed by the software program of the present invention.

It will therefore be appreciated that, using the calculations as described above, it is possible using known permeation rates of particular cryoprotectants through specific semipermeable hollow fiber membranes to design devices in accordance with the present invention with optimal sample (cell plus cryoprotectant-containing liquid) and cryoprotectant-free liquid flow rates for removal of cryoprotectant from the cryoprotectant-containing liquid, and thereby from the cell of choice. Accordingly, in yet another aspect of the present invention, a software program is provided allowing simulation of mass transport through the device of this invention. The software predicts optimal flow rates for removal of particular cryoprotectants using semipermeable hollow fiber membranes constructed of materials of known properties. Accordingly, as shown in FIG. 3, the software program of the present invention allows prediction of suitable flow rates as described above for cryoprotectant removal for any combination of cryoprotectant and hollow fiber material. Thus, the user is able to determine the optimal flow rate of cryoprotectant-containing liquid and cryoprotectant-free liquid for removal of cryoprotectant in the most efficient manner.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for removing a cryoprotectant from an interior of a cell immersed in a cryoprotectant-containing liquid, comprising the steps of:
    passing the cryoprotectant-containing liquid through at least one semipermeable hollow fiber membrane contained in a hollow module in a first direction to contact said hollow fiber membrane on at least one interior surface;
    passing a liquid which is substantially free of cryoprotectant through said hollow module in a second direction opposite to said first direction so that said cryoprotectant-free liquid contacts said semipermeable hollow fiber membrane on at least one exterior surface; and
    transferring said cryoprotectant from said cryoprotectant-containing liquid to said cryoprotectant-free liquid across a diffusion gradient between said interior surface and said exterior surface of said semipermeable hollow fiber membrane.

2. The method of claim 1, wherein said cell is contained in said cryoprotectant-containing liquid in a suspension.

3. The method of claim 1, wherein said cell is a tissue block immersed in said cryoprotectant-containing liquid.

4. The method of claim 1, wherein said cell is seeded in a porous growth matrix immersed in said cryoprotectant-containing liquid.

5. The method of claim 1, wherein said cell is grown in a monolayer on a surface matrix immersed in said cryoprotectant-containing liquid.

6. The method of claim 2, wherein said semipermeable hollow fiber membrane has a porosity of from about 50% to about 80%.

7. The method of claim 2, wherein said semipermeable hollow fiber membrane has a porosity of about 70%.

8. The method of claim 1, wherein said first flow rate is sufficient to allow transfer of cryoprotectant contained in said cryoprotectant-containing liquid from said interior surface of said semipermeable hollow fiber membrane to said exterior surface of said semipermeable hollow fiber membrane.

9. The method of claim 1, wherein said second flow rate is sufficient to substantially prevent retention of cryoprotectant on said exterior surface of said semipermeable hollow fiber membrane.

10. A method for removing a cryoprotectant from an interior of a cell immersed in a cryoprotectant-containing liquid, comprising the steps of:
    determining a membrane transfer potential of a semipermeable hollow fiber membrane for said cryoprotectant;
    calculating a first flow rate based on said membrane transfer potential for passing the cryoprotectant-containing liquid through said semipermeable hollow fiber membrane to remove said cryoprotectant from said cryoprotectant-containing liquid;

calculating a second flow rate based on said membrane transfer potential for passing a cryoprotectant-free liquid through said hollow module;

passing the cryoprotectant-containing liquid through at least one said semipermeable hollow fiber membrane contained within the hollow module at said first flow rate in a first direction to contact said hollow fiber membrane on at least one interior surface;

passing the cryoprotectant-free liquid at said second flow rate through the hollow module in a second direction opposite to said first direction so that said cryoprotectant-free liquid contacts said semipermeable hollow fiber on at least one exterior surface; and transferring said cryoprotectant from said cryoprotectant-containing liquid to said cryoprotectant-free liquid across a diffusion gradient created between said interior surface and said exterior surface of said semipermeable hollow fiber.

11. The method of claim 10, wherein said cell is contained in said cryoprotectant-containing liquid in suspension.

12. The method of claim 10, wherein said cell is contained in a tissue block immersed in said cryoprotectant-containing liquid.

13. The method of claim 10, wherein said cell is contained in a porous growth matrix immersed in said cryoprotectant-containing liquid.

14. The method of claim 10, wherein said cell is grown in monolayer culture on a solid matrix prior to immersion in said cryoprotectant-containing liquid.

15. The method of claim 10, wherein said porous hollow fiber membrane has a porosity of from about 50% to about 80%.

16. The method of claim 10, wherein said porous hollow fiber membrane has a porosity of about 70%.

17. The method of claim 1, wherein said first flow rate is sufficient to allow transfer of cryoprotectant contained in said cryoprotectant-containing liquid from said interior surface of said semipermeable hollow fiber membrane to said exterior surface of said semipermeable hollow fiber membrane.

18. The method of claim 1, wherein said second flow rate is sufficient to substantially prevent retention of cryoprotectant on said exterior surface of said semipermeable hollow fiber membrane.

* * * * *